United States Patent
Levi

(10) Patent No.: US 9,744,315 B1
(45) Date of Patent: Aug. 29, 2017

(54) SKIN TREATMENT APPARATUS

(71) Applicant: Heat In A Click LLC, Dania, FL (US)

(72) Inventor: Guy Levi, Dania, FL (US)

( * ) Notice: Subject to any disclaimer, the term of this patent is extended or adjusted under 35 U.S.C. 154(b) by 0 days.

(21) Appl. No.: 15/487,936

(22) Filed: Apr. 14, 2017

Related U.S. Application Data

(60) Provisional application No. 62/426,656, filed on Nov. 28, 2016.

(51) Int. Cl.
| | |
|---|---|
| *A61H 1/00* | (2006.01) |
| *A61H 5/00* | (2006.01) |
| *A61M 35/00* | (2006.01) |
| *A61M 11/00* | (2006.01) |
| *A61B 17/32* | (2006.01) |
| *A61B 90/30* | (2016.01) |
| *A61B 17/00* | (2006.01) |

(52) U.S. Cl.
CPC ... *A61M 11/005* (2013.01); *A61B 17/320068* (2013.01); *A61B 90/30* (2016.02); *A61B 2017/00734* (2013.01); *A61B 2017/320008* (2013.01); *A61M 2205/8206* (2013.01); *A61M 2205/8237* (2013.01)

(58) Field of Classification Search
CPC ........ A61M 11/005; A61M 2205/8206; A61M 2205/8237; A61M 35/003; A61M 37/0092; A61B 90/30; A61B 17/310068; A61B 2017/00734; A61B 2017/320008; A61B 17/54; A61B 2017/00761; A61B 2017/320004; A61B 2017/00747; A61B 2017/320012; A61B 2217/007; A45D 26/0004; A45D 2200/207; B26B 7/00; A61H 2201/0153; A61H 2205/022
See application file for complete search history.

(56) References Cited

U.S. PATENT DOCUMENTS

| | | | |
|---|---|---|---|
| 2002/0156400 A1* | 10/2002 | Babaev | A61M 11/005 601/2 |
| 2007/0293795 A1* | 12/2007 | Mr. Carroll | A61B 17/54 601/138 |

FOREIGN PATENT DOCUMENTS

WO    WO 0211813 A1 *   2/2002   ......... A45D 26/0004

OTHER PUBLICATIONS

Kingdomcares Facial Mister Atomization Nano Beauty Intrusment Eyelash Extensions Handy Mist, Amazon Product listing, eairliest posted Q and A dated Jun. 25, 2016.*
Trophy Skin Ultrasonic Skin Spatula, Amazon Product listing, earilest posted comment Mar. 1, 2014.*

* cited by examiner

*Primary Examiner* — Tatyana Zalukaeva
*Assistant Examiner* — Gabriella Burnette
(74) *Attorney, Agent, or Firm* — Frank Marino

(57) ABSTRACT

An electrical skin treating appliance has an elongate hollow polymeric housing with front and rear portions. The front portion contains a reservoir for receiving and containing water. The rear portion has one or more controls. The housing contains an ultrasonic mist generator for converting the water into a fine mist and dispersing the mist from the housing. A sonically-vibratory spatula extends from the housing at a junction of the front and rear portions and is adapted to scrape the outermost surface of a user's skin. The housing contains an oscillation generator for selectively causing ultrasonic vibration of the spatula, and the one or more controls are adapted for selectively energizing, only one at a time, the mist generator and the oscillation generator.

20 Claims, 5 Drawing Sheets

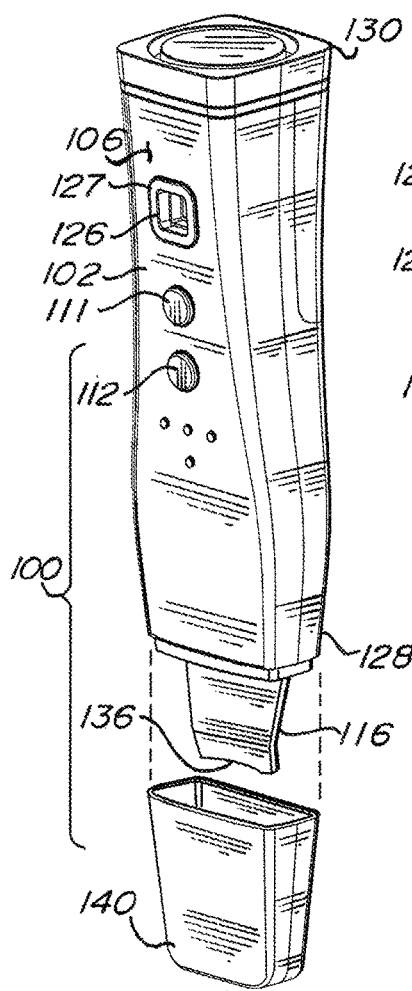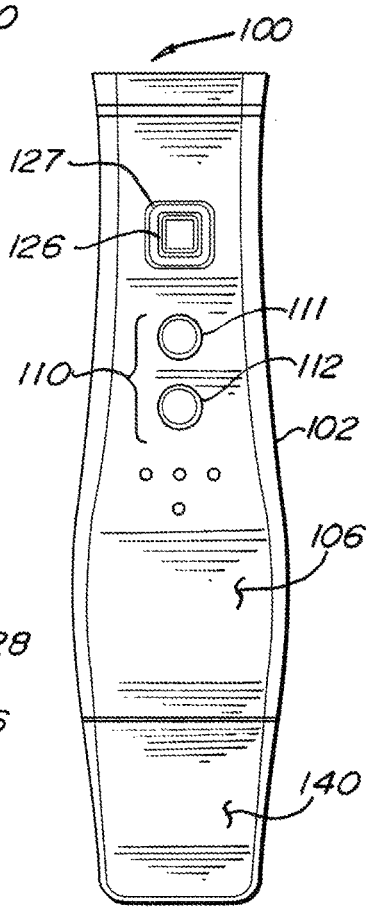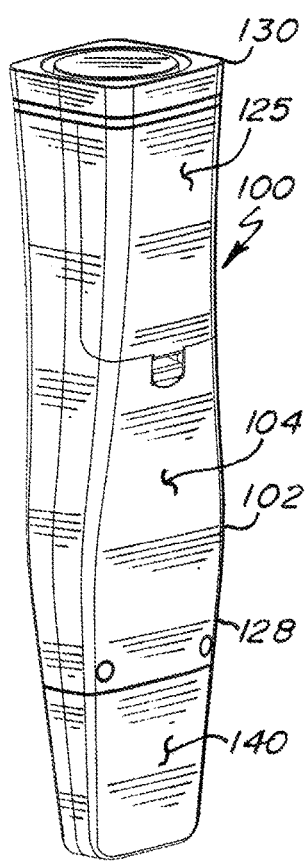
Fig.1　　Fig.2　　Fig.3
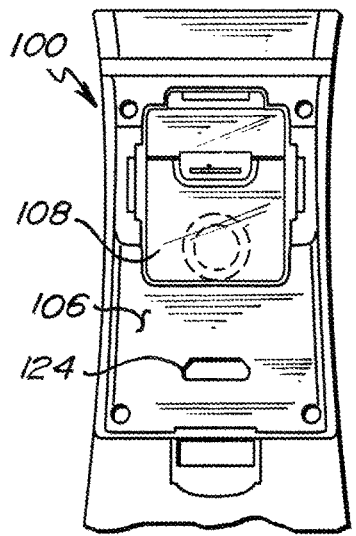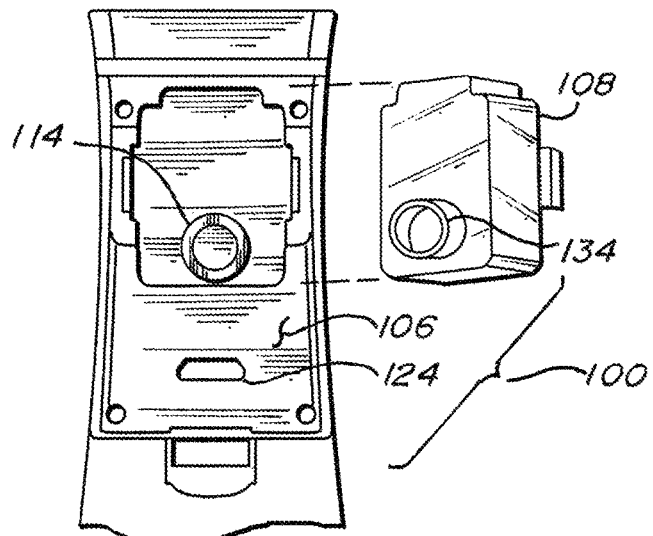
Fig.4　　Fig.5

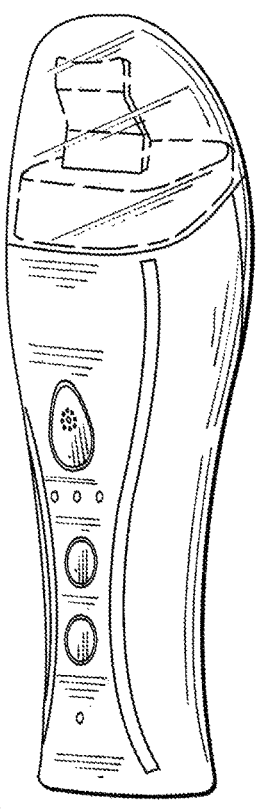
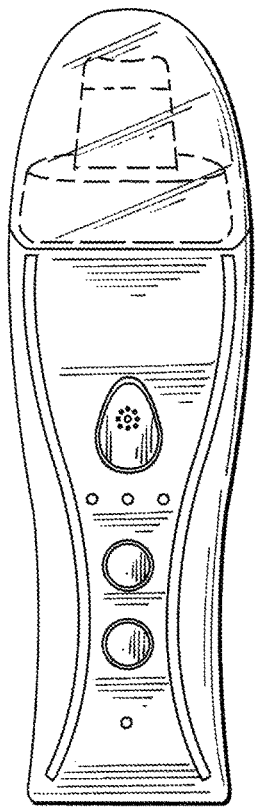
Fig.12  Fig.11
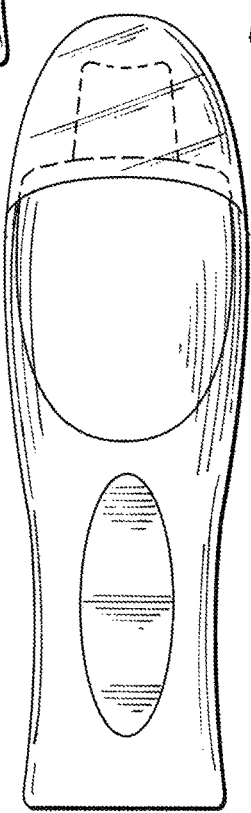
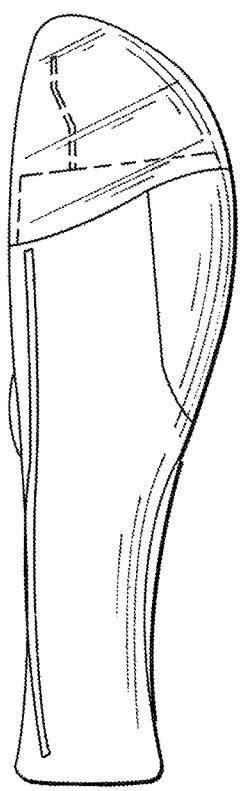
Fig.14  Fig.13

SKIN TREATMENT APPARATUS

RELATED APPLICATIONS

This application claims priority to U.S. Provisional Application No. 62/426,656, filed on 28 Nov. 2016, the entire teachings of which are incorporated herein by reference.

FIELD OF THE INVENTION

The invention is related to skin treatment and repair. More specifically, the invention is related to apparatuses and protocols for treating damaged and aged skin. In particular, the invention is related to a apparatus improves skin texture and resiliency, especially on and around the face.

BACKGROUND

Apparatuses for defoliating and rejuvenating problem skin, especially on the face, are well known, and such apparatuses but have heretofore been difficult to use and have provided unsatisfactory results.

There exists the need for means to treat problems with surface skin, and such is an object of the present invention. There exists the need to more effectively remove dead and dry surface skin, especially from the face, and such is an object of the invention. There exists the need to more effectively soften such problem skin prior to its removal, and such is an object of the invention. There exists the need to improve the visibility of such problem skin for more effective removal, and such is an object of the invention. There exists the need to lubricate such problem skin during its removal, and such is an object of the invention. There exists the need to interface more completely and efficiently with the contours of the face during the removal of such problem skin, and such is an object of the invention. Additional needs and objects are within the invention and will become obvious upon review of the included disclosure.

SUMMARY OF THE INVENTION

The invention may be embodied in or practiced using a handheld electrical apparatus for treating the skin of a user, especially in the facial area. The apparatus first wets the skin by applying a nano-mist of water or a treatment liquid, and then uses an ultrasonically-vibrated spatula to deep cleanse that skin, exfoliate it, extract impurities from it, and infuse skin treatment products into it. The spatula is vibrated at 30000 Hz to drive impurities and oils out of the pores without pain or discomfort. It causes such treatments as serums and eye creams to absorb into the skin better and work faster while maximizing the effects of such skincare products. The apparatus reduces the visibility of fine lines and wrinkles while increasing the power of the user's favorite skin care products. The apparatus harnesses the power of lower-frequency pulsations of gentle ultrasonic waves to create a noninvasive tool that better penetrates and treats the topmost layers of skin where most damage is visible. Key ingredients of the skin care products can work almost immediately instead of evaporating if applied by fingertips. Each treatment requires only approximately 180 seconds and provides almost instant results.

The invention may be embodied in or practiced using a skin treating apparatus with a housing containing a reservoir for receiving and containing water or a suitable treatment, an ultrasonic mist generator for converting the water or treatment into a fine mist and dispersing the mist from the housing, an ultrasonically-vibratory spatula extending from the housing and adapted to scrape the outermost surface of a user's skin; an oscillation generator for selectively causing ultrasonic vibration of the spatula; and a battery for selectively energizing, only one at a time, the mist generator and the oscillation generator. The battery may be rechargeable and the housing may include a connector in electrical communication with the rechargeable battery for receiving an external battery charger. The reservoir may be removable from the housing, remotely fillable, and replaceable into the housing. The mist may be dispersed from a nozzle disposed on the housing and in liquid communication with the reservoir. The housing may be elongate and have a distal end and a proximal end and the spatula may be disposed at the distal end and the nozzle at or near the proximal end. The ultrasonic mist generator may be an atomizer to aerosolize the water, and the mist may be the aerosolized water. The reservoir may have a water outlet, and the nozzle, atomizer, and water outlet may be in linear alignment. The spatula may be a thin metallic blade extending substantially longitudinally from the distal end. The spatula may have s a concave distal edge. A cover may be engageable with the housing to enclose the spatula and movable relative thereto to expose the spatula.

The invention may also be embodied in or practiced using an electrical skin treating appliance having an elongate hollow polymeric housing of front and rear portions. The front portion may contain a reservoir for receiving and containing water. The rear portion may have one or more controls. An ultrasonic mist generator may be contained by the housing for converting the water into a fine mist and dispersing the mist from the housing. An ultrasonically-vibratory spatula may extend from the housing at a junction of the front and rear portions and may be adapted to scrape the outermost surface of a user's skin. An oscillation generator may be contained by the housing for selectively causing ultrasonic vibration of the spatula. One the one or more controls adapted for selectively energizing, only one at a time, the mist generator and the oscillation generator may be provided. The housing may contain a rechargeable battery in electrical communication with the one or more controls, and a connector in electrical communication with the rechargeable battery for receiving an external battery charger. The reservoir may be removable from the housing, remotely fillable, and replaceable into the housing. The mist may be dispersed from a nozzle disposed on the rear portion and in liquid communication with the reservoir. The housing may have a distal end and a proximal end and the spatula may be disposed at the distal end and the nozzle at or near the proximal end. The ultrasonic mist generator may be an atomizer to aerosolize the water, and the mist may be the aerosolized water. The reservoir may have a water outlet, and the nozzle, atomizer, and water outlet may be in linear alignment. The spatula may be a thin metallic blade extending substantially longitudinally from the distal end. The spatula may have a concave distal edge. A polymeric cover may be engageable with the housing to enclose the spatula and removable there-from to expose the spatula.

Further features and aspects of the invention are disclosed with more specificity in the Detailed Description and Drawings provided herein and showing exemplary embodiments of the invention.

BRIEF DESCRIPTION OF THE DRAWINGS

Exemplary embodiments of skin treatment apparatuses in accordance with or useful in practicing the invention are shown in the accompanying Drawings, of which;

FIG. 1 is a front perspective view of a first exemplary skin treatment apparatus with its cover being removed;

FIG. 2 is a front view of the apparatus of FIG. 1;

FIG. 3 is a rear perspective view of the apparatus of FIG. 1;

FIG. 4 is a view of the water reservoir of the apparatus of FIG. 1, having its reservoir cover removed;

FIG. 5 is a view of the water tank being removed from the apparatus of FIG. 1;

FIG. 11 a front perspective view of a second exemplary skin treatment apparatus;

FIG. 12 a front view of the apparatus of FIG. 11;

FIG. 13 is a side view of the apparatus of FIG. 11; and

FIG. 14 is rear view of the apparatus of FIG. 11.

DETAILED DESCRIPTION OF EXEMPLARY EMBODIMENTS

Figure 6:
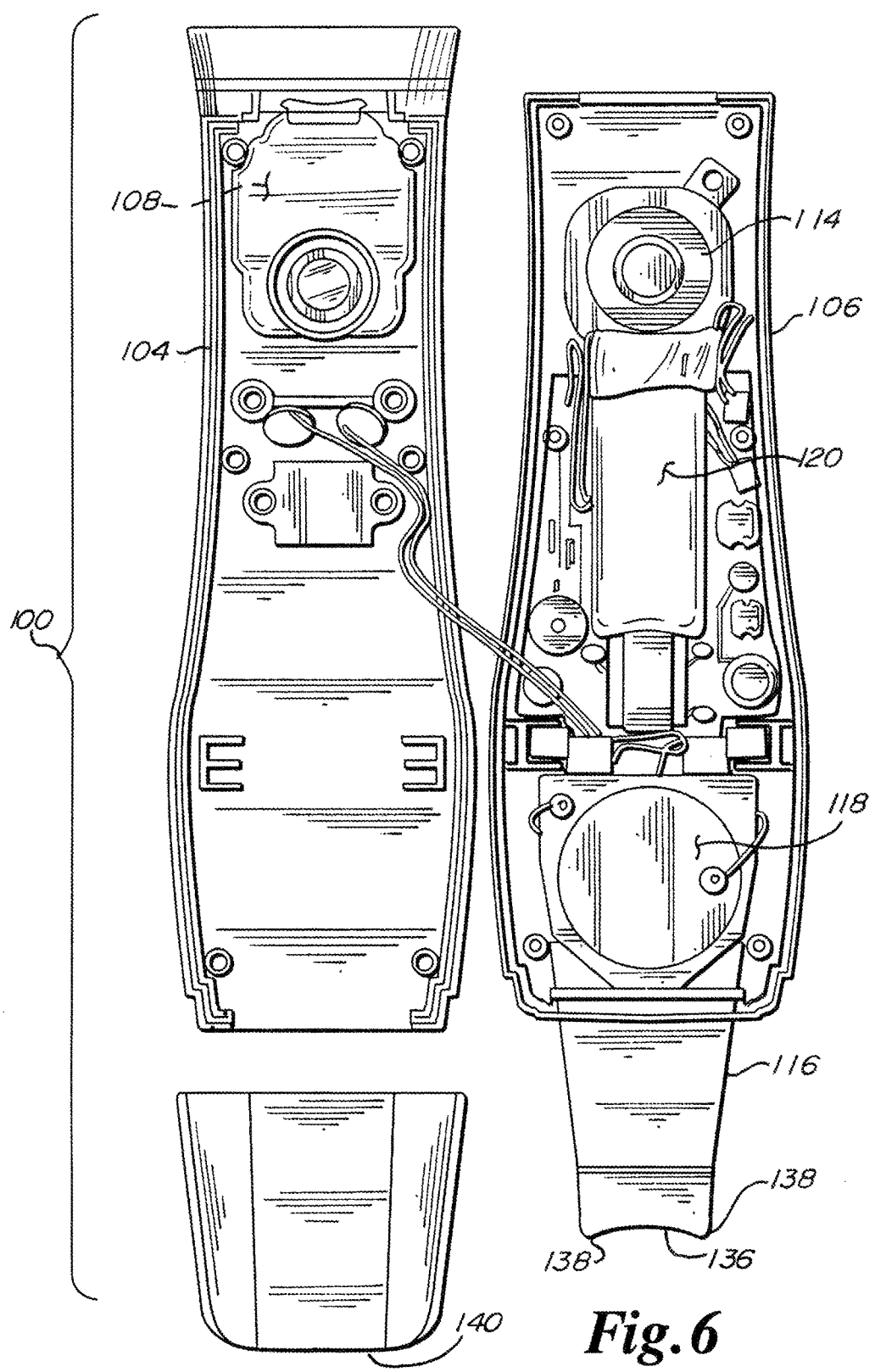
FIG. 6 is a view of the apparatus of FIG. 1 with its front and rear portions taken apart.
Figure 7:
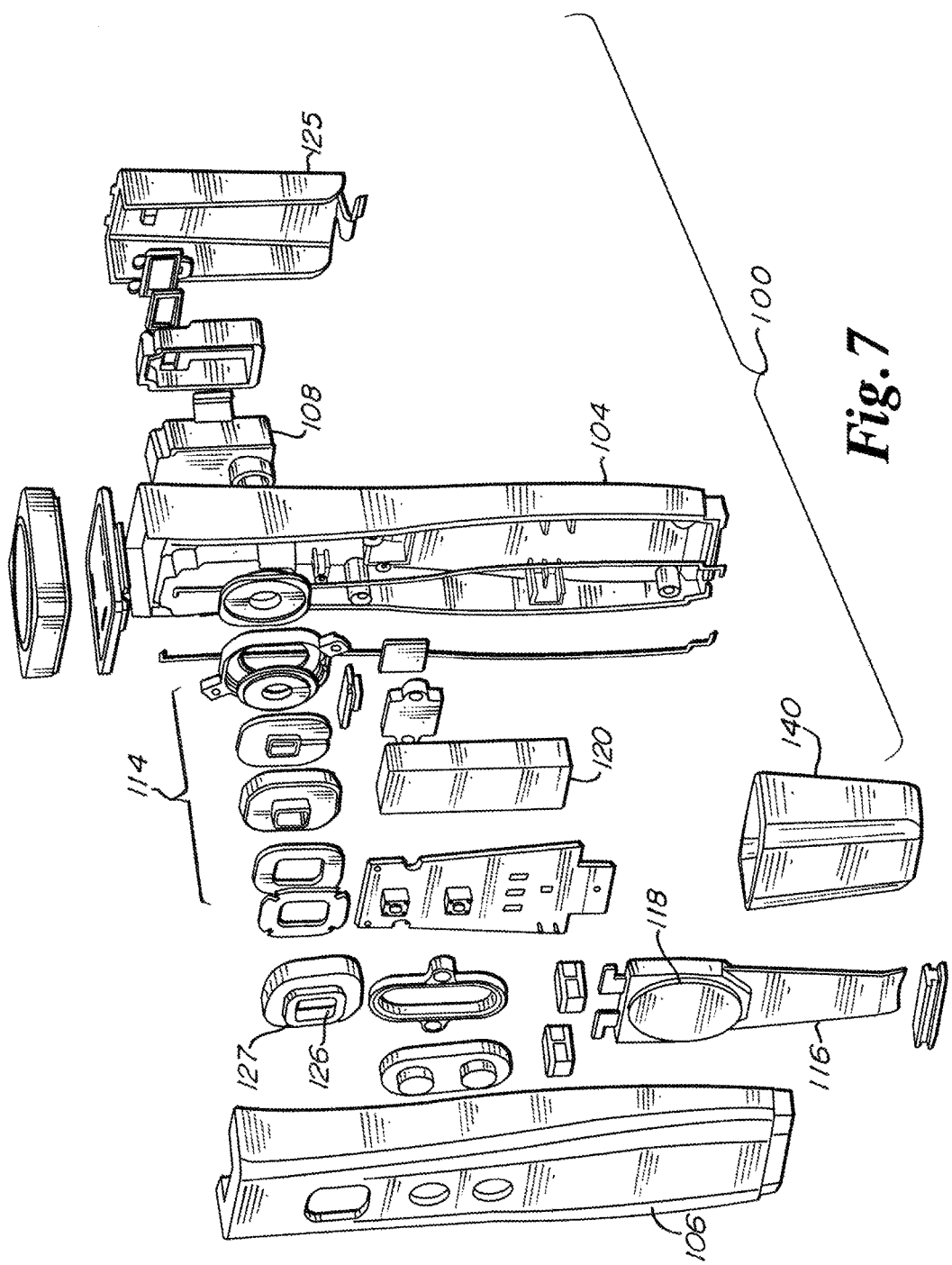
FIG. 7 is an exploded view of the apparatus of FIG. 1.

As appreciated by review of the included drawings, the invention may be embodied in or practiced using handheld apparatuses 100 or 200, which are both capable of providing skin-wetting and vibratory skin scraping in a manner that interfaces most effectively with the various types and contours of facial skin.

Referring to FIGS. 1 through 10, the first electrical handheld apparatus 100 is shown, having an elongate hollow polymeric housing 102 comprising a front portion 104 and a rear portion 106. The front portion contains a reservoir 108 for receiving and containing water or an atomizable skin-treating essence. The rear portion has controls 110 for controlling the electrical functions of the device. The controls include a mist switch 111 and a vibration switch 112.

Figure 8:
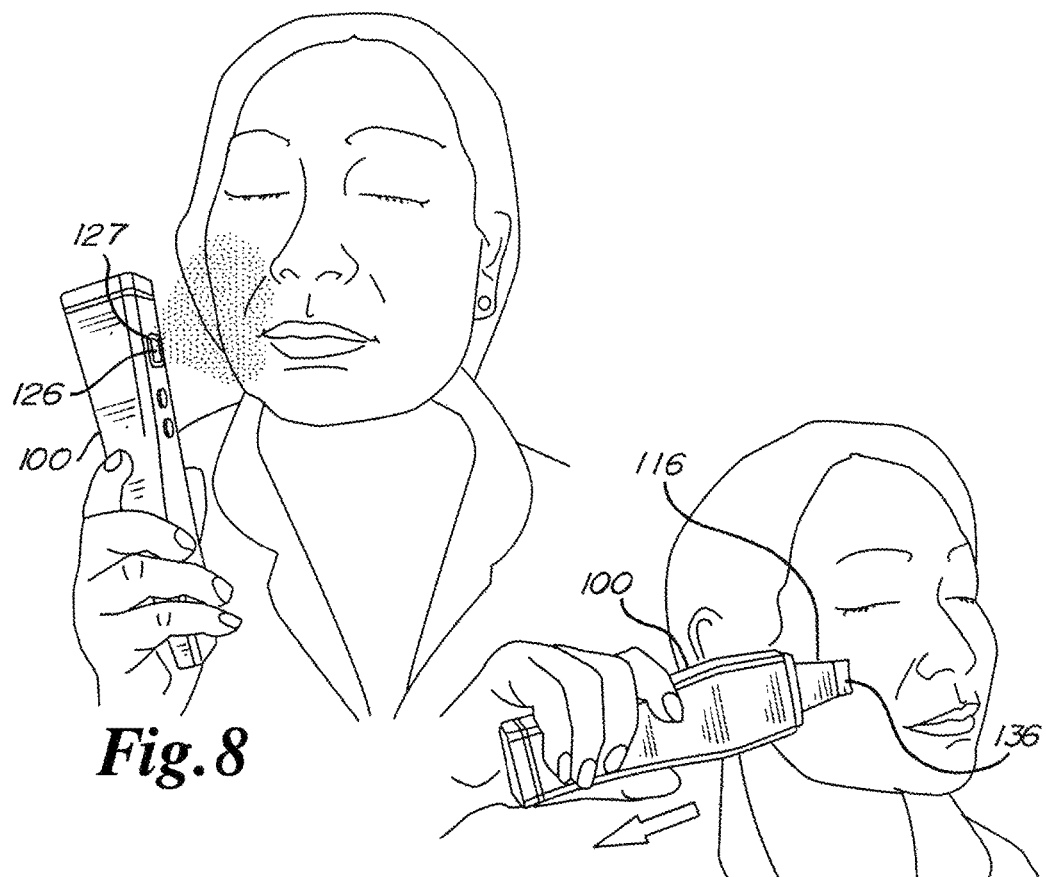
FIG. 8 is a view of the device of FIG. 1 during misting of a user's face.
Figure 9:
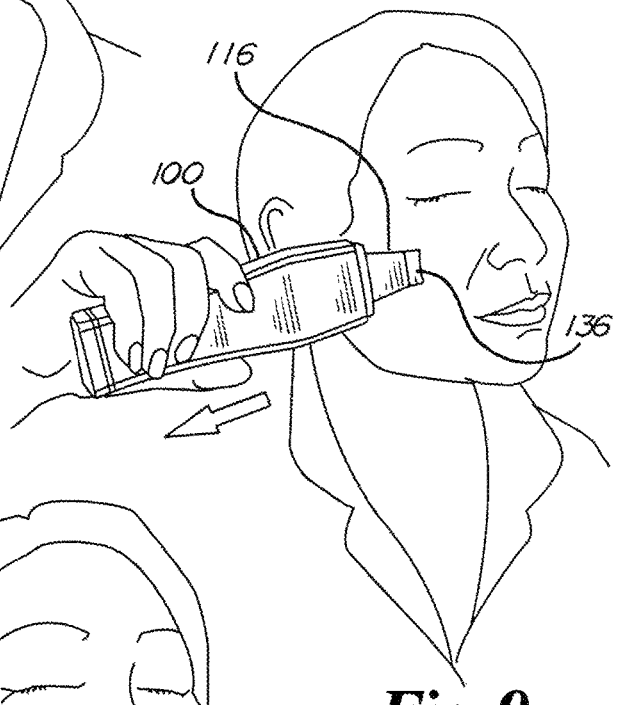
FIG. 9 is a view of the device of FIG. 1 during back-scraping of the user's face.
Figure 10:
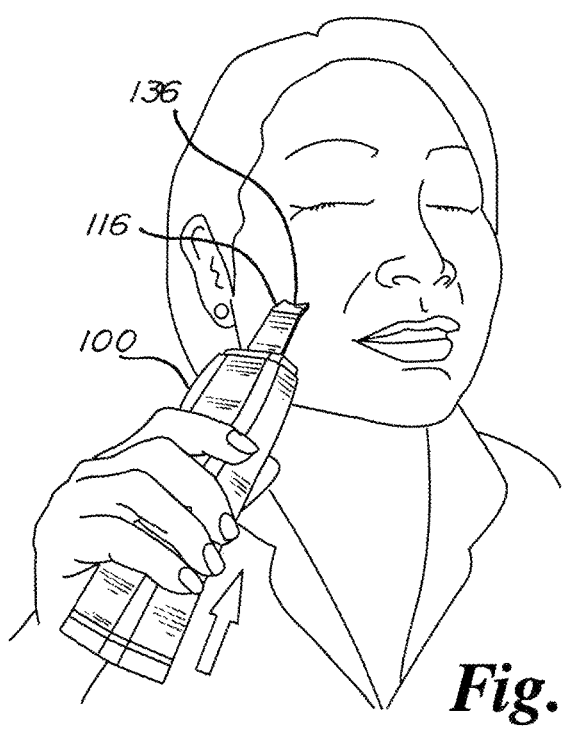
FIG. 10 is a view of the device of FIG. 1 during fore-scraping of the user's face.

An ultrasonic mist generator 114 is contained within the housing and selectively converts the water or essence into a fine mist and disperses the mist from the housing, as seen in FIG. 8. A ultrasonically-vibratory spatula 116 extends from the housing at a junction of the front and rear portions and is adapted to scrape the outermost surface of a user's skin, by either a pulling action, as seen in FIG. 9, or a pushing action, as seen in FIG. 10.

An oscillation generator 118 contained by the housing selectively causes ultrasonic vibration of the spatula. The controls selectively energize, only one at a time, the mist generator and the oscillation generator.

The housing contains a rechargeable battery 120 in electrical communication with the controls, and a connector 124 in electrical communication with the rechargeable battery for receiving an external battery charger (not shown). The reservoir is removable from the housing, as seen in FIGS. 4 and 5, so that it may be filled remotely, and replaced into the housing. A removable panel 125 covers the reservoir and electrical connector.

The mist is dispersed from a nozzle 126 disposed on the rear portion and in liquid communication with the reservoir. The nozzle is surrounded by an annular LED 127 which lights when the mist generator is energized, to illuminate the skin that is to be wetted by the mist, which is found to greatly assist application of the mist.

The housing has a distal end 128 and a proximal end 130. The spatula is disposed at the distal end and the nozzle is disposed near to the proximal end.

The ultrasonic mist generator is an atomizer. Such atomizers are will known and commonly used in such devices as ultrasonic humidifiers and inhalers. As an example, the disclosure of the atomizer of U.S. Pat. No. 5,021,701 is incorporated herein by reference. The ultrasonic generator aerosolizes the water, so that mist is aerosolized water. The reservoir has a water outlet 134. The nozzle, atomizer, and water outlet are in linear alignment.

As seen in the Figures, the spatula is a thin metallic blade extending substantially longitudinally from the distal end. The spatula has a concave distal scraping edge 136 with rounded corners 138, which is found to be most effective for interfacing with the wide variety of skin contours on the human face. A polymeric cover 140 is engageable with the housing to enclose the spatula and removable there-from to expose the spatula, as seen in FIG. 1.

FIGS. 11 through 13 depict a second apparatus 200, which is constructed and which functions the same as the first embodiment, except features an ornamental design distinct there-from.

In use, the mist switch is first activated, which causes the LED to light and mist to flow from the nozzle. The mist is then applied to those areas of the skin intended to be treated, until that skin is fully wetted. This softens the skin, and also provided lubricity for scraping. The mist switch is then deactivated, and the vibration switch is activated, to cause the spatula to vibrate at a high ultrasonic frequency. The scraping edge is then gently pressed against the wetted skin and either pulled or pushed to scrape away dead skin, extract, expel blackheads, and increase blood circulation to invigorate the skin. Repeated activation of the vibration button cycles the oscillator through low frequency, high frequency, and pulsation.

While the invention has been shown and described with reference to specific exemplary embodiments, it should be understood by those skilled in the art that various changes in form and detail may be made without departing from the spirit and scope of the invention, and that the invention should therefore only be limited according to the following claims, including all equivalent interpretation to which they are entitled.

I claim:

1. A skin treating apparatus comprising;
   a housing containing a reservoir for receiving and containing water;
   an ultrasonic mist generator for converting the water into a fine mist and dispersing the mist from the housing;
   a ultrasonically-vibratory spatula extending from the housing and adapted to scrape the outermost surface of a user's skin;
   an oscillation generator for selectively causing ultrasonic vibration of the spatula; and
   a battery for selectively energizing, only one at a time, the mist generator or the oscillation generator.

2. The skin treating apparatus of claim 1 wherein the battery is rechargeable and the housing further comprises a connector in electrical communication with the rechargeable battery for receiving an external battery charger.

3. The skin treating apparatus of claim 2 wherein the reservoir is removable from the housing, remotely fillable, and replaceable into the housing.

4. The skin treating apparatus of claim 3 wherein the mist is dispersed from a nozzle disposed on the housing and in liquid communication with the reservoir.

5. The skin treating apparatus of claim 4 wherein the housing is elongate and comprises a distal end and a proximal end and wherein the spatula is disposed at the distal end and the nozzle is disposed at or near the proximal end.

6. The skin treating apparatus of claim 5 wherein the ultrasonic mist generator comprises an atomizer to aerosolize the water, and the mist comprises the aerosolized water.

7. The skin treating apparatus of claim 6 wherein the reservoir comprises a water outlet; and the nozzle, atomizer, and water outlet are in linear alignment.

8. The skin treating apparatus of claim 5 wherein the spatula is a thin metallic blade extending substantially longitudinally from the distal end.

9. The skin treating apparatus of claim 8 wherein the spatula comprises a concave distal edge.

10. The skin treating apparatus of claim 9 further comprising a cover engageable with the housing to enclose the spatula and movable relative thereto to expose the spatula.

11. An electrical skin treating appliance comprising;
an elongate hollow polymeric housing comprising front and rear portions, the front portion containing a reservoir for receiving and containing water; the rear portion comprising one or more controls;
an ultrasonic mist generator contained by the housing for converting the water into a fine mist and dispersing the mist from the housing;
a ultrasonically-vibratory spatula extending from the housing at a junction of the front and rear portions and adapted to scrape the outermost surface of a user's skin;
an oscillation generator contained by the housing for selectively causing ultrasonic vibration of the spatula; and wherein
the one or more controls are adapted for selectively energizing, only one at a time, the mist generator or the oscillation generator.

12. The electrical skin treating appliance of claim 11 wherein the housing further contains a rechargeable battery in electrical communication with the one or more controls; and the housing further comprises a connector in electrical communication with the rechargeable battery for receiving an external battery charger.

13. The electrical skin treating appliance of claim 12 wherein the reservoir is removable from the housing, remotely fillable, and replaceable into the housing.

14. The electrical skin treating appliance of claim 13 wherein the mist is dispersed from a nozzle disposed on the rear portion and in liquid communication with the reservoir.

15. The electrical skin treating appliance of claim 14 wherein the housing comprises a distal end and a proximal end and wherein the spatula is disposed at the distal end and the nozzle is disposed at or near the proximal end.

16. The electrical skin treating appliance of claim 15 wherein the ultrasonic mist generator comprises an atomizer to aerosolize the water, and the mist comprises the aerosolized water.

17. The electrical skin treating appliance of claim 16 wherein the reservoir comprises a water outlet; and the nozzle, atomizer, and water outlet are in linear alignment.

18. The electrical skin treating appliance of claim 11 wherein the spatula is a thin metallic blade extending substantially longitudinally from the distal end.

19. The electrical skin treating appliance of claim 18 wherein the spatula comprises a concave distal edge.

20. The electrical skin treating appliance of claim 19 further comprising a polymeric cover engageable with the housing to enclose the spatula and removable there-from to expose the spatula.

* * * * *